(12) United States Patent
Li

(10) Patent No.: US 10,610,445 B2
(45) Date of Patent: Apr. 7, 2020

(54) TESTICLE MASSAGER

(71) Applicant: Hui Li, Jiangsu (CN)

(72) Inventor: Hui Li, Jiangsu (CN)

( * ) Notice: Subject to any disclaimer, the term of this patent is extended or adjusted under 35 U.S.C. 154(b) by 246 days.

(21) Appl. No.: 15/557,790

(22) PCT Filed: Mar. 10, 2016

(86) PCT No.: PCT/CN2016/076026
§ 371 (c)(1),
(2) Date: Jan. 5, 2018

(87) PCT Pub. No.: WO2016/141880
PCT Pub. Date: Sep. 15, 2016

(65) Prior Publication Data
US 2018/0193221 A1   Jul. 12, 2018

(30) Foreign Application Priority Data
Mar. 12, 2015 (CN) .......................... 2015 1 0108072

(51) Int. Cl.
*A61F 5/00* (2006.01)
*A61H 19/00* (2006.01)
*A61H 23/02* (2006.01)
*A61F 5/41* (2006.01)

(52) U.S. Cl.
CPC .......... *A61H 19/32* (2013.01); *A61H 23/0263* (2013.01); *A61F 2005/417* (2013.01); *A61H 2201/165* (2013.01); *A61H 2201/5005* (2013.01)

(58) Field of Classification Search
CPC .......... A61H 19/00; A61H 19/30; A61H 19/32
USPC ....................................... 600/38–41
See application file for complete search history.

(56) References Cited

U.S. PATENT DOCUMENTS

| | | | |
|---|---|---|---|
| 4,488,541 A | 12/1984 | Garcia | 128/79 |
| 5,397,294 A | 3/1995 | Hwang | 601/71 |
| 6,790,189 B2 * | 9/2004 | Kobayashi | A61F 5/41 600/38 |
| 8,641,600 B2 * | 2/2014 | Nelson | A61F 5/41 600/38 |

FOREIGN PATENT DOCUMENTS

| | | | |
|---|---|---|---|
| CN | 2206105 | 8/1995 | ............. A61H 19/00 |
| CN | 2274953 | 2/1998 | ............. A61H 19/00 |
| CN | 2352162 | 12/1999 | ............. A61H 19/00 |
| CN | 101785739 | 7/2010 | ............. A61H 19/00 |
| CN | 103356373 | 10/2013 | ............. A61H 19/00 |
| CN | 204521500 | 8/2015 | ............. A61H 19/00 |

* cited by examiner

*Primary Examiner* — John P Lacyk
(74) *Attorney, Agent, or Firm* — Hayes Soloway P.C.

(57) ABSTRACT

A device for massaging male testicles, includes a control part, a vibration part, a bendable part and wherein all the parts can be attached to a human body after being assembled together so as to massage testicles in a vibration manner. The device is convenient and labor-saving to use; and massaging testicles by utilizing the device can improve sperm and secretion of male sex hormones, thereby promoting physical health.

16 Claims, 4 Drawing Sheets

TESTICLE MASSAGER

FIELD OF THE INVENTION

The present invention relates to an appliance for promoting the health of male reproductive system by massaging testicles.

BACKGROUND OF THE INVENTION

The inventor filed an invention patent application relating to handheld testicle massager in 2012, the application No. of which is 201210097337X. However, the inventor has found in practice that usually the testicles must be massaged for 20 minutes or longer time to achieve good effect. It is tiring and inconvenient for hands to press the instrument to massage testicles for such a long time.

Contents of the Invention

The object of the present invention is to provide a novel testicle massage device, which enables the user to massage his testicles conveniently.

The object of the present invention is achieved as follows: the testicle massager comprises a vibration part and a control part, etc., wherein, the control part can control the vibration of the vibration part, and the testicle massager further includes a bendable part that may be attached to a human body. The vibration part, the control part and the bendable part are assembled together.

As an improvement to the scheme described above, the bendable part is made of a soft material.

As an improvement to the scheme described above, the bendable part may be tightened up and attached to scrotum, so as to apply force to the testicles.

As an improvement to the scheme described above, the bendable part can be kept attached to the human body once it is tightened up and attached to the scrotum, without fixing it by a hand.

As an improvement to the scheme described above, the bendable part may be wrapped around the root part of the scrotum near the human body in entirety or in part.

As an improvement to the scheme described above, the bendable part may be wrapped around the root part of the male external genital organs (including penis, scrotum and testicles) near the trunk in entirety or in part, and may be arranged between the testicles and the trunk. Thus, the entire device may be fixed to the root part of the penis.

As an improvement to the scheme described above, the testicle massager includes a massage head with protrusions, and all or a part of the protrusions can exert pressure to the scrotum and testicles.

As an improvement to the scheme described above, the testicle massager includes a massage head with protrusions, and all or a part of the protrusions can exert pressure to the scrotum and testicles.

As an improvement to the scheme described above, the bendable part may be made in a shape of pants. The vibration part may be placed at a position near the testicles.

The bendable part is not limited in quantity, which is to say, there may be one or more bendable parts, or one bendable part may be divided into several sections.

In order to limit the positions of the testicles along the axial direction of the penis, skirts that are not parallel to the penis in axial direction may be added on two sides of the bendable part.

The bendable part may be made of a material such as cloth, elastic band, or soft rubber, etc., and the relative position of the bendable part may be fixed with any other common fixing means, such as a magic tape or buckle.

In order to facilitate fixing the testicles in position, the bendable part may have a shape with varying radial dimension, such as a cone shape.

The vibration part may be a common vibration part, such as an eccentric motor, a flat vibrating motor, or a button-type vibrating motor, etc.

The massager may be powered by a built-in rechargeable battery, an ordinary dry battery, or other power supply.

The device provided in the present invention has the following advantages: the product provided in the present invention can be kept attached to the human body when it is used, without fixing it by a hand, and the user even can massage testicles when wearing trousers. Therefore, the product provided in the present invention is labor saving and much more convenient.

DESCRIPTION OF THE DRAWINGS

Hereunder the present invention will be further described with reference to the accompanying drawings and examples.

In FIG. 1: 1—set-top box; 2—strap; 3—electric wire; 4—motor fixing plate; 5—button-type vibrating motor; 6—fixing back plate;

In FIG. 2: 7—strap; 8—strap; 9—back plate of set-top box;

In FIG. 4: 10—massage head;

In FIG. 5: 11—strap; 12—strap;

In FIG. 8: 13—penis; 14—strap; 15—abdomen of human body; 16—strap; 17—testicle

Embodiments

Figure 1:
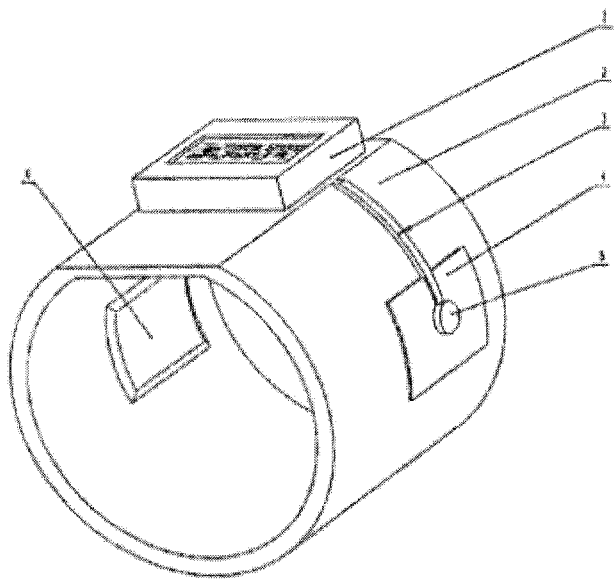
FIG. 1 is a three-dimensional view of the assembly in example 1 of the present invention.

The example 1 is an embodiment of the present invention. In the example shown in FIG. 1: control parts (control circuit, LCD screen, buttons, etc.) are mounted in a set-top box 1, and the set-top box may also include a power supply (e.g., a rechargeable battery or dry battery), or may be connected to external power supply. The control circuit is connected with a button-type vibrating motor 5 (vibration part) through electric wires 3. Thus, the control part can control the vibration of the vibration part. The button-type vibrating motor 5 is mounted in a motor fixing plate 4, a strap 2 (i.e., the bendable part described above) is clamped between a motor fixing plate and a fixing back plate (a pair of motor fixing plate and fixing back plate exists on the left and on the right respectively in the figure), and the vibration contact area on the strap can be increased by means of the two plates. The motor fixing plate and the fixing back plate can be fixed together by screws. The strap may be made of a soft or elastic material, such as elastic band, emulsion, silica gel, or plastic, etc. In order to fix the device to the root part of the penis conveniently, the strap 2 may be made in a shape that has a smaller diameter at one side.

The control circuit can adjust the movement parameters, including vibration frequency, amplitude, and time, etc.

The example 2 is another embodiment of the present invention. The example 2 is essentially the same as the example 1. The set-top box back plate 9 and the set-top box clamp the strap 8 between them, and can be fixed by screws. A difference lies in: the example 2 has two straps, i.e., strap 7 and strap 8.

Figure 2:
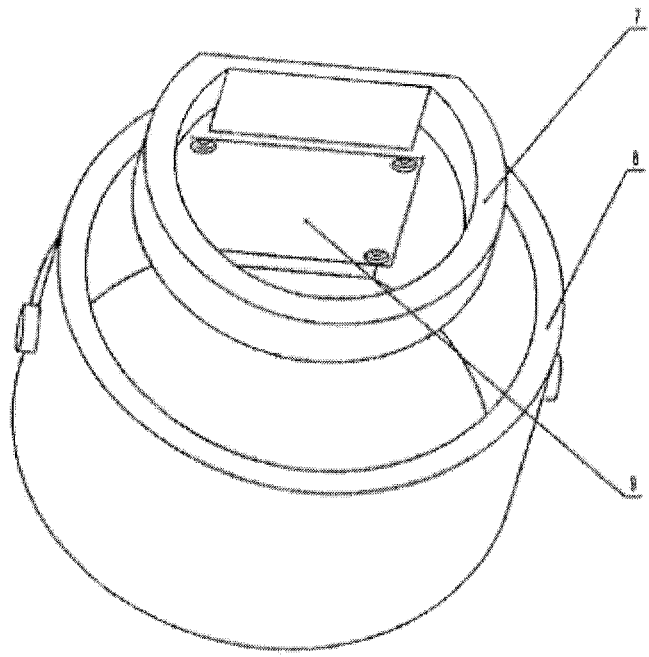
FIG. 2 is a three-dimensional view of the assembly in example 2 of the present invention.
Figure 3:
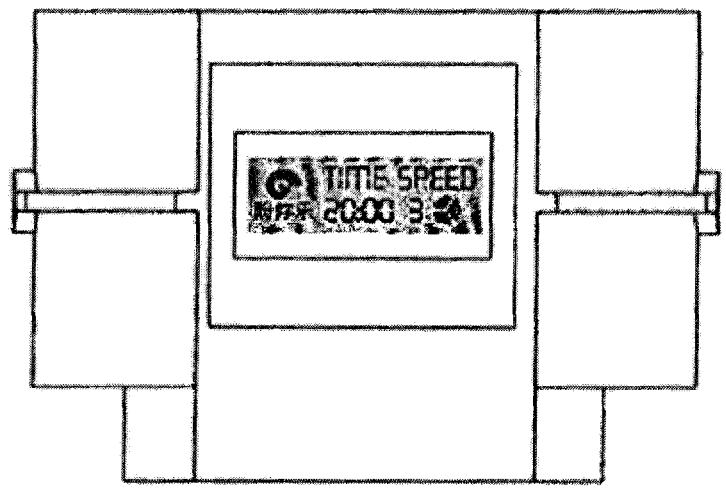
FIG. 3 is a top view of the assembly in example 2 of the present invention.
Figure 4:
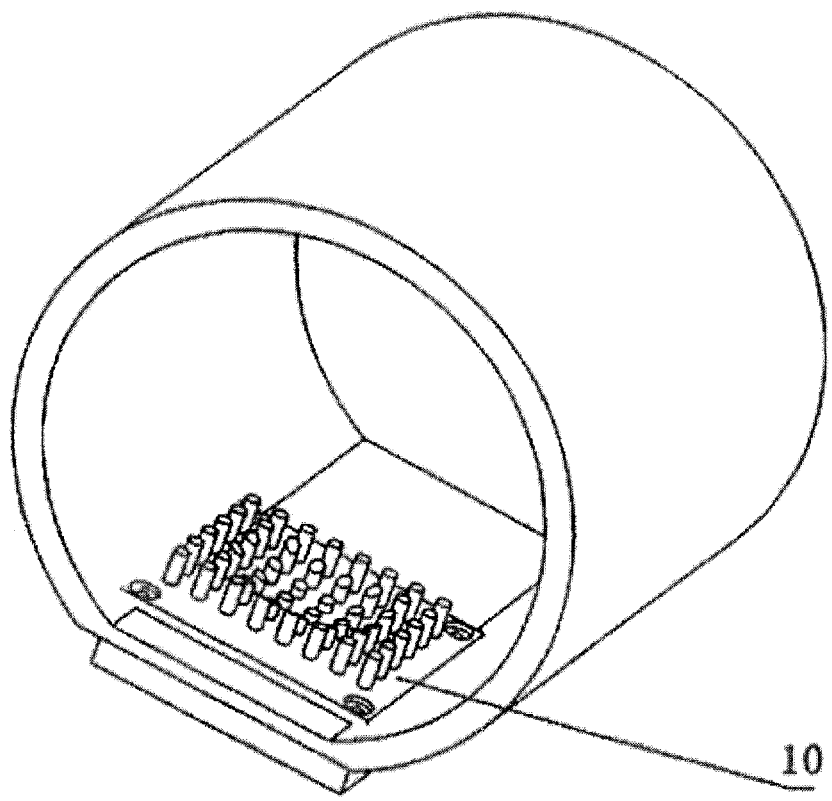
FIG. 4 is a three-dimensional view of the assembly in example 3 of the present invention.
Figure 8:
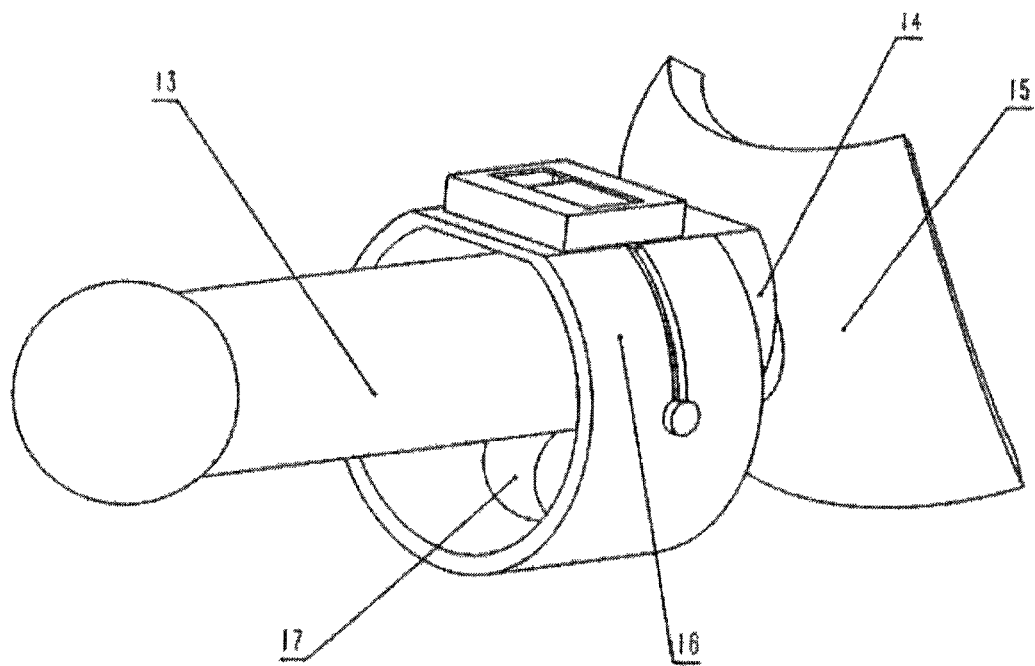
FIG. 8 is a front three-dimensional view of example 2 of the present invention during use.
Figure 9:
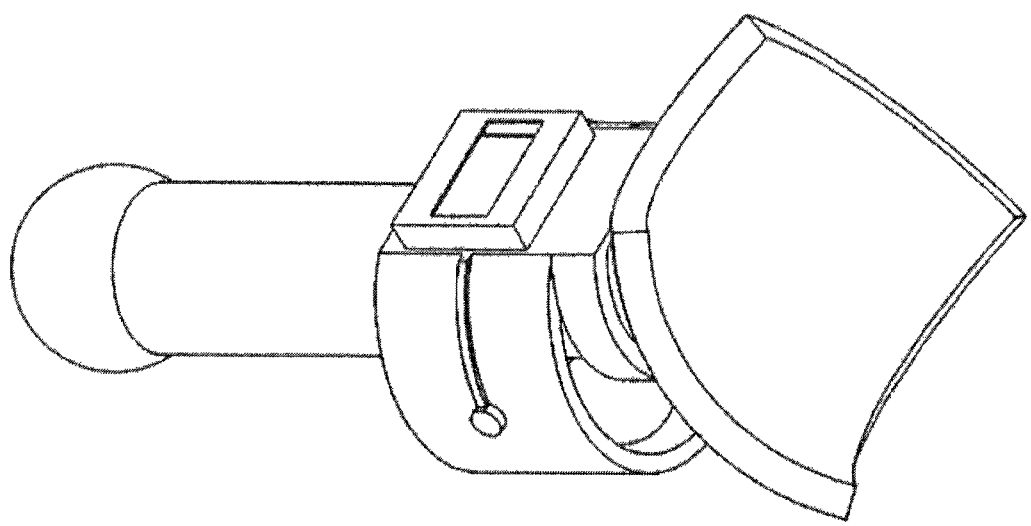
FIG. 9 is a rear three-dimensional view of example 2 of the present invention during use.

The use state of the example is shown in FIGS. 8 and 9. In FIG. 8, the strap 16 (the same as the strap 8 in FIG. 2) wraps the penis 13, testicles 17, and scrotum tightly. The strap 14 (the same as the strap 7 in FIG. 2) is fixed to the root part of the penis, so that the entire device will not fall off. When the button-type vibrating motor vibrates, the entire strap 16 will be driven to vibrate, and thereby drives the testicles to vibrate together and massage the testicles. The restriction situation of the strap 14 to the root part of the penis can be seen in FIG. 9.

The example 3 is another embodiment of the present invention. In this embodiment, the testicle massager includes a massage head 10 that has protrusions for pressing the scrotum and testicles. Of course, alternatively the massage head may be arranged at a different position on the strap shown in the figure. The massage head may be made of a soft material, which wraps the testicles after it is bent. The tops of the protrusions on the message head are advantageously arranged into a concave arc surface so as to accommodate the testicles, especially when the massage head is made of a hard material.

Figure 5:
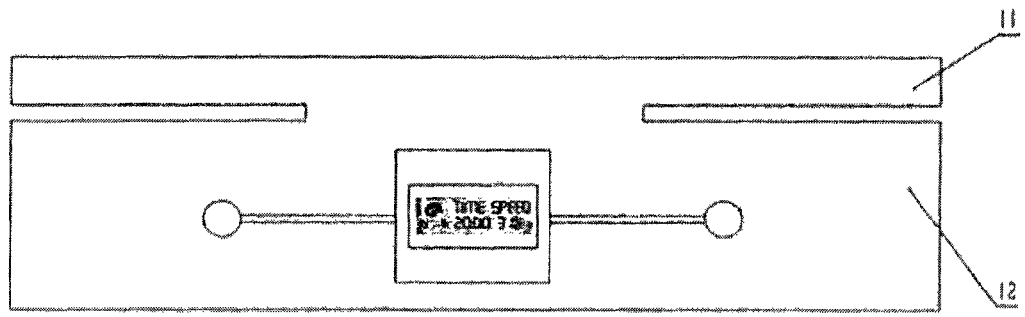
FIG. 5 is a top view of the assembly in example 4 of the present invention.
Figure 6:
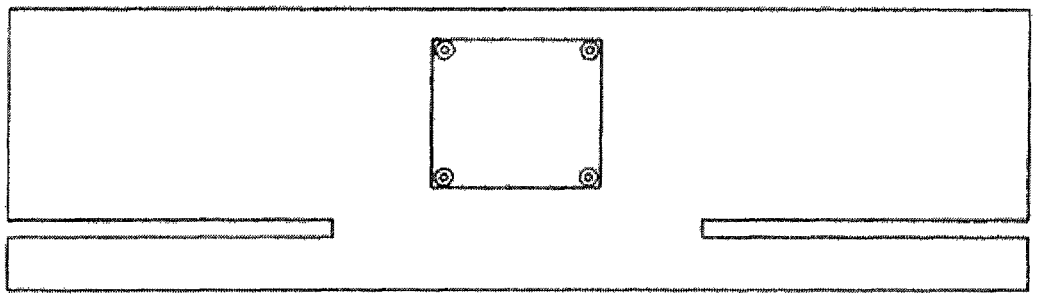
FIG. 6 is a bottom view of the assembly in example 4 of the present invention.
Figure 7:
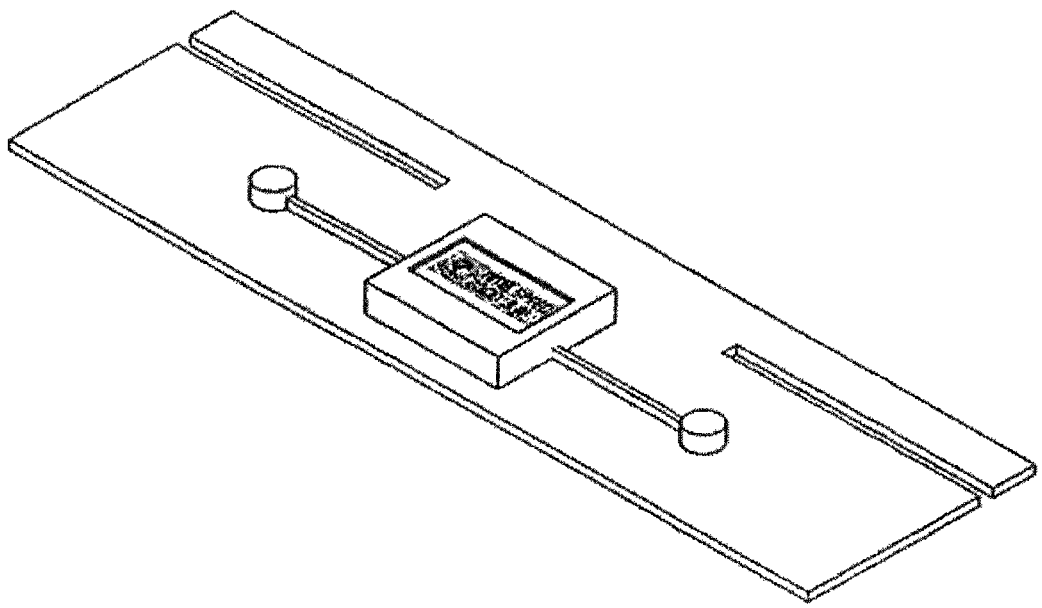
FIG. 7 is a three-dimensional view of the assembly in example 4 of the present invention.

The example 4 is another embodiment of the present invention. As shown in FIG. 5, in this embodiment, the bendable part (straps 11 and 12) is made of cloth, and magic tapes are stitched to the cloth, so that the strap 12 can wrap the penis, testicles and scrotum tightly, while the strap 11 wraps the root part of the penis tightly. The use state is similar to the state shown in FIG. 8.

Alternatively, the bendable part may be made in a shape of pants, and the vibration part and the massage head are placed on the place where the pants contact with the testicles. Thus, another novel example is formed. The structure is not shown in the figures, since it can be easily imagined by the person skilled in the art.

In the above examples, common parts (e.g., power supply, etc.) are not shown for the convenience of drawing. In the figures, the bendable part is referred to as "strap". The set-top box, electric wires, and vibration motor, etc., are similar to those shown in FIG. 1, and are not labeled in other figures.

The invention claimed is:

1. A testicle massager configured to be worn by a male animal, said testicle massager comprising a strap system comprising a first strap formed of a soft bendable material and configured to be wrapped around a penis of a wearer, and a second strap also formed of a soft bendable material, longer than the first strap, and configured to be wrapped around the testicles and scrotum of the wearer, and a vibrator and a controller for controlling vibration of the vibrator, supported by the strap system.

2. The testicle massager according to claim 1, wherein the second strap is configured to be tightened and attached to the wearer's scrotum.

3. The testicle massager according to claim 1, wherein the first strap is configured to be wrapped around a root part of male external genital organs near the wearer's trunk, between the wearer's testicles and the wearer's trunk.

4. The testicle massager according to claim 1, wherein the testicle massager includes a massage head having a plurality of protrusions configured to press and contact the scrotum of the wearer, wherein all or a part of the plurality of protrusions are configured to exert pressure to the scrotum and testicles of the wearer when the testicle massager is worn.

5. A testicle massager configured to be worn by a male animal, said testicle massager comprising a vibrator and a controller for controlling vibration of the vibrator, wherein the testicle massager includes a first strap configured to be wrapped around a penis of the wearer, and a second strap, longer than the first strap, supporting the vibrator, the controller and a massage head having a plurality of protrusions, configured to wrap around in part and to press and contact the scrotum of the wearer, wherein all or a part of the plurality of protrusions are configured to exert pressure to the scrotum and testicles of the wearer.

6. A testicle massager, comprising a vibrator, a massage head, and a controller for controlling vibration of the vibrator, wherein the massage head has a curved surface configured to accommodate the scrotum of the wearer.

7. The testicle massager according to claim 1, wherein the massage head has a curved surface configured to accommodate the scrotum of the wearer.

8. The testicle massager according to claim 6, wherein the massage head curved surface has protrusions extending therefrom.

9. The testicle massager according to claim 1, wherein the testicle massager has a curved massage head configured to accommodate the scrotum of the wearer.

10. The testicle massager according to claim 9, wherein the curved massage head has protrusions extending therefrom.

11. The testicle massager according to claim 2, wherein the testicle massager has a curved massage head configured to accommodate the scrotum of the wearer.

12. The testicle massager according to claim 11, wherein the curved massage head has protrusions extending therefrom.

13. The testicle massager according to claim 11, wherein the testicle massager has a curved massage head configured to accommodate the scrotum of the wearer.

14. The testicle massager according to claim 13, wherein the curved massage head has protrusions extending therefrom.

15. The testicle massager according to claim 6, wherein the massage head includes a bendable element configured to be tightened up and attached to the scrotum of the wearer.

16. The testicle massager according to claim 6, wherein the massage head includes a bendable element configured to be wrapped at least in part around a root of a penis of the wearer.

* * * * *